United States Patent [19]
Baur et al.

[11] Patent Number: 4,939,246
[45] Date of Patent: Jul. 3, 1990

[54] PURIFICATION OF LONG-CHAIN ALKYLGLUCOSIDES

[75] Inventors: Richard Baur, Mutterstadt; Jochen Houben, Ludwigshafen; Hans-Ulrich Jaeger, Neustadt; Alfred Oftring, Bad Durkheim; Johannes Perner, Neustadt, all of Fed. Rep. of Germany

[73] Assignee: BASF Aktiengesellschaft, Ludwigshafen, Fed. Rep. of Germany

[21] Appl. No.: 309,150

[22] Filed: Feb. 13, 1989

[30] Foreign Application Priority Data

Feb. 13, 1988 [DE] Fed. Rep. of Germany ....... 3804599

[51] Int. Cl.⁵ .......................... C07G 3/00; C07H 1/00; C07H 1/06
[52] U.S. Cl. .................................. 536/18.6; 536/124; 536/127; 536/18.5
[58] Field of Search ...................... 536/18.6, 124, 127, 536/18.5

[56] References Cited
U.S. PATENT DOCUMENTS

| | | | |
|---|---|---|---|
| 3,219,656 | 11/1965 | Boettner | 536/18.6 |
| 3,547,828 | 12/1970 | Mansfield | 536/4.1 |
| 3,598,865 | 8/1971 | Lew | 536/18.6 |
| 3,839,318 | 10/1974 | Mansfield | 536/18.6 |
| 4,349,669 | 9/1982 | Klahr et al. | 536/127 |
| 4,820,814 | 4/1989 | Lueders | 536/18.6 |

Primary Examiner—Ronald W. Griffin
Assistant Examiner—Everett White
Attorney, Agent, or Firm—Oblon, Spivak, McClelland, Maier & Neustadt

[57] ABSTRACT

Long-chain alkylglucosides are purified by extraction with water from reaction mixtures obtainable by reacting monosaccharides and alcohols of 8 or more carbon atoms or by transacetalating short-chain alkylglucosides with alcohols of 8 or more carbon atoms, adjusted to a pH above 6 in either case.

9 Claims, No Drawings

PURIFICATION OF LONG-CHAIN ALKYLGLUCOSIDES

BACKGROUND OF THE INVENTION

Long-chain alkylglucosides, ie. alkylglucosides where the alkyl chain numbers 8 or more carbon atoms, are used in industry as nonionic surfactants of high wetting power, for example in highly alkaline industrial cleansers. They are also increasingly used as constituents in skin and hair care agents. This use, however, requires particularly pure products.

Long-chain alkylglucosides are prepared for example by reacting monosaccharides, or reducing sugars which are hydrolyzable to monosaccharides, and alcohols of 8 or more carbon atoms in the presence of acidic catalysts. However, short-chain alkylglucosides, for example $C_1$–$C_6$-alkylglucosides, can also be transacetalated with alcohols of 8 or more carbon atoms in the presence of acidic catalysts. In either case, however, an appreciable excess of long-chain alcohol is required. The products are thus always reaction mixtures consisting of the long-chain alkylglucoside and the excess long-chain alcohol. The long-chain alkylglucoside must be isolated from these mixtures since otherwise, if the long-chain alkylglucosides are used in aqueous media, unclear solutions are formed. Processes for preparing long-chain alkylglucosides are known; cf. for example U.S. Pat. Nos. 3,219,656, 3,598,865, 3,839,318 and 3,547,828.

To isolate the long-chain alkylglucoside from the reaction mixture, the practice has been to distill off the long-chain alcohol at around 140° C. under much reduced pressure. The high thermalstress on the alkylglucoside gives rise to resinification and increasingly, especially with alkyl glucosides having comparatively long chains, to the formation of dark products.

U.S. Pat. No. 3,547,828 discloses the purification of neutralized mixtures of long-chain alkylglucosides and long-chain alcohols by treating the mixtures with acetone. However, such a method of purification is very expensive to practice in industry. German Laid-Open Application DOS 3,001,064 discloses a process for purifying $C_8$–$C_{16}$-alkylglucosides obtained by reacting short-chain alkylglucosides or hydroxyalkylglucosides with $C_8$–$C_{16}$-alcohols in the presence of acidic catalysts. In this process, the reaction mixture is neutralized and the long-chain alcohol is separated off by distillation, the distillative removal of at least the last fractions of unconverted long-chain alcohol being carried out in the presence of glycols whose boiling points are not more than 10° C. above and not more than 30° C. below the boiling points of the long-chain alcohols to be separated off. It is true that the addition of glycol brings about a reduction in the viscosity of the mixture to be purified by distillation, but on the other hand it requires the removal of the added glycol. U.S. Pat. No. 3,839,318 also discloses separating the excess long-chain alcohol from mixtures of long-chain alcohols and long-chain alkylglucosides by means of a solvent. The solvent used is for example heptane. However, this process has the disadvantage that it requires the additional use of a solvent which needs to be recovered.

SUMMARY OF THE INVENTION

It is an object of the present invention to provide a gentle process for purifying long-chain alkylglucosides which is less costly and resource-intensive to carry out than existing processes.

We have found that this object is achieved according to the invention by a process for purifying a long-chain alkylglucoside by extraction from a reaction mixture obtainable by reacting a monosaccharide and an alcohol of 8 or more carbon atoms or by transacetalating a $C_1$–$C_6$-alkylglucoside with an alcohol of 8 or more carbon atoms and in either case adjusted brought to a pH above 6 by extracting the long-chain alkylglucoside from the reaction mixture by means of water. The extraction may be carried out continuously or batchwise.

DETAILED DESCRIPTION OF THE PREFERRED EMBODIMENTS

The long-chain alyklglucoside is prepared as described above in the account of the prior art. Suitable reducing monosaccharides are for example pentoses or hexoses or compounds which are hydrolyzable to such monosaccharides. Examples of suitable monosaccharides are glucose, manose, galactose, talose, allose, altrose, idose, arabinose, xylose, ribose and lyxose and also mixtures thereof. The reducing sugars which are hydrolyzable to monosaccharides include for example oligosaccharides and polysaccharides, such as maltose, lactose, sucrose, raffinose, dextrins, starches, corn syrup and xylose. However, glucose is preferred.

The abovementioned starting materials can be reacted in the presence of customary acidic catalysts directly with alcohols which have 8 or more carbon atoms in the molecule. The long-chain alcohols customarily contain from 8 to 32, preferably from 12 to 18, carbon atoms. Preference is given to using technical-grade mixtures of long-chain alcohols from the oxo or Ziegler process. Mixtures of $C_{10}/C_{16}$-, $C_{12}/C_{14}$-and $C_{12}$–$C_{18}$-alcohols are particularly readily obtainable industrially and therefore preferred for the preparation of long-chain alkylglucosides.

As mentioned above, it is of advantage for the preparation of long-chain alkylglucosides first to prepare short-chain alkylglucosides, for example by reacting a monosaccharide with a monohydric $C_3$–$C_5$-alcohol, and then to subject the short-chain alkylglucosides to a transacetalation by adding long-chain monohydric alcohols. The preparation of the glucoside and transacetalation each take place in the presence of an acidic catalyst. According to German Laid-Open Application DOS 3,232,791, the preparation of the short-chain alkylglucoside may be carried out in the presence of, for example, sodium perborate as a cocatalyst. All the abovementioned processes give rise to glycosides or glucoside mixtures containing major proportions of unconverted long-chain alcohol, since an excess of the alcohol over the sugar during the reaction is unavoidable because of the otherwise likely self-condensation and the undesirably high proportion of oligosaccharide associated therewith. The amounts of long-chain alcohol used, based on the weight, are within the range from 1.2:1 to 10:1, preferably from 1.8:1 to 2.0:1. The reaction mixtures obtained in each case, which contain an acidic catalyst, are brought to a pH above 6 by adding a base. This pH is determined by for example preparing a 50% strength solution of the reaction mixture in water and performing the measurement at 20° C. The pH of the reaction mixture is preferably adjusted to within the range from 7.5 to 9. The only important thing is to avoid a pH within the strongly acid range, since such conditions combined with the temperatures required for the extraction bring about a partial hydrolysis of the alkylglucoside.

According to the invention, the long-chain alkylglucoside is extracted from the neutralized reaction mixture by means of water.

The amount of water required is from 0.5 to 4, preferably from 2 to 3, parts by volume of water per part by volume of reaction mixture. The water used is preferably demineralized. The temperature of the reaction mixture in the course of the extraction is not more than 100° C., preferably within the range from 40 to 60° C. In general, the extraction is carried out at from 50 to 55° C. The extraction may be performed one or more times, for example 2-4 times, by dividing the above-specified amount of water into appropriate portions. If continuous-working equipment is available, the extraction may also be carried out continuously. Since when the reaction mixture is treated with water an emulsion may form, it is advisable that the apparatus for a continuous process be a mixer-settler battery. Should an emulsion form in the course of the batchwise extraction of the reaction mixture, it may be broken by adding a customary demulsifier.

The aqueous alkylglucoside solution isolated from the reaction mixture may be either used directly in the form of the aqueous solution or distilled to remove the water, if an anhydrous alkylglucoside is desired. The aqueous alkylglucoside solution obtained on extraction with water, however, can also be subjected to more thorough purification, for example to an extraction with an organic solvent. Suitable organic solvents are for example the short-chain alcohols distilled out of the reaction mixture in the course of the preparation of the long-chain alkylglucoside, provided the alkylglucoside is prepared by transacetalation. The short-chain alcohol usable as or addable to the solvent not only serves as a solvent for the longer-chain alcohol but also has an emulsion-inhibiting and foam-suppressing effect. The treatment of the aqueous alkylglucoside solution with an organic solvent, for example a $C_2$–$C_6$-alcohol, permits a further purification of the extracted aqueous alkylglucoside solution to remove residual longer-chain alcohol. The alcohol-treated aqueous alkylglucoside solution is additionally subjected to a brief steam distillation in order to remove residual amounts of entrained long-chain alcohol and to distill off azeotropically the short-chain alcohol used for the purification.

Whereas existing processes for purifying reaction mixtures of long-chain glucosides and long-chain alcohols by distillation employ pressures below 1 mbar and temperatures of up to 140° C., in the process according to the invention pressures as high as 50 mbar are sufficient to effect purification, so that in total a far lower level of investment in hardware is required. In the preparation of the alkylglucoside it presents no problem to use a longer-chain alcohol, for example a $C_{20}$–$C_{32}$-alcohol, for the subsequent removal from the reaction mixture. Whereas in existing processes for purification by distillation the boiling point of the long-chain alcohol and the heat sensitivity of the long-chain alkylglucoside impose a limit on purification options, disqualifying particularly long-chain alcohols, for example $C_{20}$–$C_{30}$-alcohols, from the preparation of surfactants, it is possible in the process according to the invention, and presents no problem, to separate even these long-chain alkylglucosides from the particularly long-chain alcohols in a simple manner. As a result, the preparation of more hydrophobic long-chain alkylglucosides in pure form is significantly simpler.

EXAMPLE

Preparation of long-chain alkylglucoside

In a reaction vessel equipped with a stirrer and a water separator, 1500 ml (16 mol) of n-butanol, 855 g (4.5 mol) of anhydrous dextrose, 200 ml of toluene and 7.5 g of p-toluenesulfonic acid are refluxed for one hour, during which 24 ml (1.33 mol) of water are separated off. 15 g of sodium perborate are then added, and water is separated out of the reaction mixture for a further 2 hours (32 ml corresponding to 1.8 mol). 1000 ml of an n-butanol/toluene mixture are then distilled off under a pressure of 180 mbar. 1500 ml of a technical-grade alcohol mixture of $C_{12}$–$C_{18}$-alcohols are then added, the pressure is reduced to 60 mbar, and for the next 2 hours at 80° C. and then for 1 hour at a base of column temperature of 100° C. the n-butanol formed in the transacetalation is distilled off.

Extraction of the reaction mixture

The above-described reaction mixture is cooled down to 60° C. and neutralized with 10 g of sodium acetate and 10 g of sodium carbonate to pH 7.5 To extract the long-chain alkylglucoside present therein, 2 l of water are added, the mixture is stirred at 45° C. for 20 minutes, and the stirrer is switched off. The mixture separates into two phases. The bottom phase, which contains the bulk of the long-chain glucoside, is separated off. The alkylglucoside concentration is 26% by weight. The top phase is then admixed with 2 l of water and 200 ml of the n-butanol/toluene mixture obtained at the transacetalation stage of the preparation of the long-chain alkylglucoside. This mixture is stirred at 50° C. for 20 minutes. It is then allowed to settle at that temperature. The bottom, aqueous phase is separated off, and the top phase is admixed once more with 2 l of water and 500 ml of the distilled-off n-butanol/toluene mixture, and stirred at 55° C. for 20 minutes, and the phases are separated. The remaining top phase is freed azeotropically under a water separator from emulsified water and, following replenishment with fresh long-chain alcohol, it is used in the preparation of long-chain alkylglucoside.

The aqueous phases obtained in the course of the extraction are each concentrated under a pressure of 50 mbar and at 80° C., then subjected to a steam distillation at 80° C. (2 l of distillate) and bleached by adding 15 g of sodium perborate. Water is added to standardize the solids content of 50% by weight of alkylglucoside. In this way 1875 g of an aqueous solution of long-chain alkylglucoside are obtained.

We claim:

1. A process for purifying a long-chain alkylglucoside by extraction from a reaction mixture, obtained (i) by reacting a monosaccharide and an alcohol of 8 or more carbon atoms or (ii) by transacetalating a $C_1$–$C_6$-alkylglucoside with an alcohol or 8 or more carbon atoms, and in either case, adjusted to a pH above 6, which process comprises extracting the long-chain alkylglucoside from said reaction mixture with water, wherein one part by volume of said reaction mixture is extracted with from 0.5 to 4 parts by volume of water.

2. The process of claim 1, wherein said reaction mixture being extracted has a pH of from 7.5 to 9.

3. The process of claim 1, wherein said reaction mixture is extracted continuously 2 to 4 times.

4. The process of claim 1, wherein said extraction is carried out at a temperature of from 40 to 60° C.

5. The process of claim 1, wherein said monosaccharide is glucose, manose, galactose, talose, allose, altrose, idose, arabinose, xylose, ribose, lyxose, or a mixture thereof.

6. The process of claim 1, wherein said alcohol contains from 8 to 32 carbon atoms.

7. The process of claim 1, wherein said alcohol contains from 12 to 18 carbon atoms.

8. The process of claim 1, wherein one part by volume of said reaction mixture is extracted with from 2 to 3 parts by volume of said water.

9. The process of claim 1, wherein said extraction is carried out at a temperature of from 50 to 55° C.

* * * * *